US011085889B2

(12) United States Patent
Kucharczyk

(10) Patent No.: US 11,085,889 B2
(45) Date of Patent: Aug. 10, 2021

(54) PROTECTION DEVICE FOR AN AREA DETECTOR

(71) Applicant: RIGAKU CORPORATION, Tokyo (JP)

(72) Inventor: Damian Kucharczyk, Wroclaw (PL)

(73) Assignee: RIGAKU CORPORATION, Tokyo (JP)

( * ) Notice: Subject to any disclaimer, the term of this patent is extended or adjusted under 35 U.S.C. 154(b) by 106 days.

(21) Appl. No.: 16/574,306

(22) Filed: Sep. 18, 2019

(65) Prior Publication Data

US 2020/0096458 A1 Mar. 26, 2020

(30) Foreign Application Priority Data

Sep. 20, 2018 (EP) .................................... 18195713

(51) Int. Cl.
*G01N 23/20* (2018.01)
*G01N 23/20008* (2018.01)

(52) U.S. Cl.
CPC .............................. *G01N 23/20008* (2013.01)

(58) Field of Classification Search
CPC ......... G01N 23/20008; G01N 2223/30; G01N 23/04; G01N 23/083; G01N 2223/1006; G01N 2223/1013; G01N 2223/1016; G01N 2223/106; G01N 2223/3303; G01N 2223/631; G01N 23/05; G01N 23/203; G01N 2223/308; G01N 2223/301; G01N 2223/32; G01N 2223/321; G01N 2223/618; G01N 23/046; G01N 33/02; A61B 6/102; A61B 5/055; A61B 6/032; A61B 6/037;

(Continued)

(56) References Cited

U.S. PATENT DOCUMENTS 5,056,365 A 10/1991 Gray et al.
5,097,495 A 3/1992 Gray et al.
(Continued)

FOREIGN PATENT DOCUMENTS

WO    WO 2018/136582 A1    7/2018

OTHER PUBLICATIONS

European Search Report of EP 18 19 5713.5 dated Apr. 2, 2019.

*Primary Examiner* — Irakli Kiknadze
(74) *Attorney, Agent, or Firm* — Birch, Stewart, Kolasch & Birch, LLP

(57) ABSTRACT

A protection device (100) and a method for protecting an area detector (200) against collision with an object (10). The protection device (100) is designed to be mountable on the area detector (200) and includes a mounting frame (120) configured to be mounted on the area detector (200) to be protected, wherein the mounting frame (120) is designed to at least partially cover a perimeter rim surface of the area detector (200) to be protected; a first sensor unit arranged on the mounting frame (120) and a light curtain (147, 148) configured to detect and signal a potential collision of the object (10) is provided at an inner area of the area detector (200) surrounded by the mounting frame. A second sensor unit is arranged on the mounting frame (120) and included at least one sensor configured to detect and signal a potential collision of the object (10) at a perimeter rim area of the area detector (200). Further provided is an X-ray detector system and X-ray analysis system including the protection device (100).

20 Claims, 8 Drawing Sheets

(58) Field of Classification Search
CPC ....... A61B 6/467; A61B 6/5294; A61B 6/548;
A61B 6/4441; A61B 6/4405; A61B
6/4458; A61B 6/4452; A61B 6/4464;
A61B 6/4476; A61B 6/4482; A61B
6/0407; A61B 6/54; A61B 6/4429; A61B
6/4423; A61B 6/0487; A61B 6/589; A61B
6/105; A61B 5/0064; A61B 6/4241; A61B
5/004; A61B 5/702; A61B 6/04; A61B
6/4258; A61B 6/4266; A61B 6/4275;
A61B 6/5205; A61B 6/08; A61B 6/56;
A61B 6/06; A61B 6/42; A61B 6/5229;
A61B 6/547; A61B 6/588; A61B
2090/376; A61B 6/03; A61B 6/4085;
A61B 2034/107; A61B 2090/033; A61B
2090/3612; A61B 2090/365; A61B
2090/371; A61B 2090/3764; A61B
2562/0219; A61B 6/14; A61B 2090/064;
A61B 2090/065; A61B 6/00; A61B
6/145; A61B 6/502; A61B 90/06; A61B
90/20; A61B 6/4233; A61B 2034/2048;
A61B 2034/2051; A61B 2034/2055;
A61B 2090/366; A61B 2090/372; A61B
2090/3762; A61B 2090/3966; A61B
34/30; A61B 5/0062; A61B 5/0077; A61B
6/035; A61B 6/4435; A61B 6/107; A61B
6/4007; G01V 8/20; A61G 2203/36;
A61G 2203/44; A61G 2203/726; A61G
7/018; A61G 7/10; A61G 2203/72; A61G
13/08; A61G 2203/12; A61N 2005/1061;
G21K 1/025; G21K 1/046; H01J
2237/024; H01J 37/023; H01J 37/265;
H01J 37/28; H04L 67/12; H04L 67/1097;
H04L 1/0002; H04L 1/0041; H04L 1/18;
H04L 5/0064; H04L 1/0009; H04L
1/1874; H04L 67/306; H04L 29/00; H04L
47/28; H04L 67/125; H04L 12/10; H04L
1/0057; H04L 1/0076; H04L 1/187; H04L
2209/38; H04L 2209/805; H04L 41/00;
H04L 41/0672; G01T 1/1648; G01T
1/2985; G01T 1/166; G01T 1/1642; G01T
1/1603; G01T 1/1611; G01T 1/1614;
G01T 1/1635; G01T 1/1615; G01T 7/08;
G01T 1/00; G01T 1/2018; G06T 11/006;
G06T 2211/424; G06T 2211/436; A61K
38/00; A61K 9/0014; A61K 9/0019;
A61K 9/0031; A61K 9/0048; A61K
9/0053; A61K 9/006; A61K 9/0078;
A61K 9/06; G05B 19/0461; G05B
2219/45169; G05B 2219/49143; H05G
1/08; H05G 1/26; G01L 9/008; H02J
7/345
USPC .............. 378/62, 196–198, 205–207, 70–74
See application file for complete search history.

(56) References Cited

U.S. PATENT DOCUMENTS

| | | | |
|---|---|---|---|
| 5,486,700 A | 1/1996 | Silberklang et al. | |
| 7,470,896 B2 | 12/2008 | Pawlak et al. | |
| 2004/0263865 A1 | 12/2004 | Pawlak et al. | |
| 2006/0039537 A1* | 2/2006 | Strobel | G01N 23/04 378/197 |
| 2006/0067475 A1 | 3/2006 | Bauch et al. | |
| 2008/0279333 A1* | 11/2008 | Sattler | A61B 6/102 378/98.2 |
| 2009/0278702 A1* | 11/2009 | Graumann | A61B 34/20 340/686.2 |

* cited by examiner

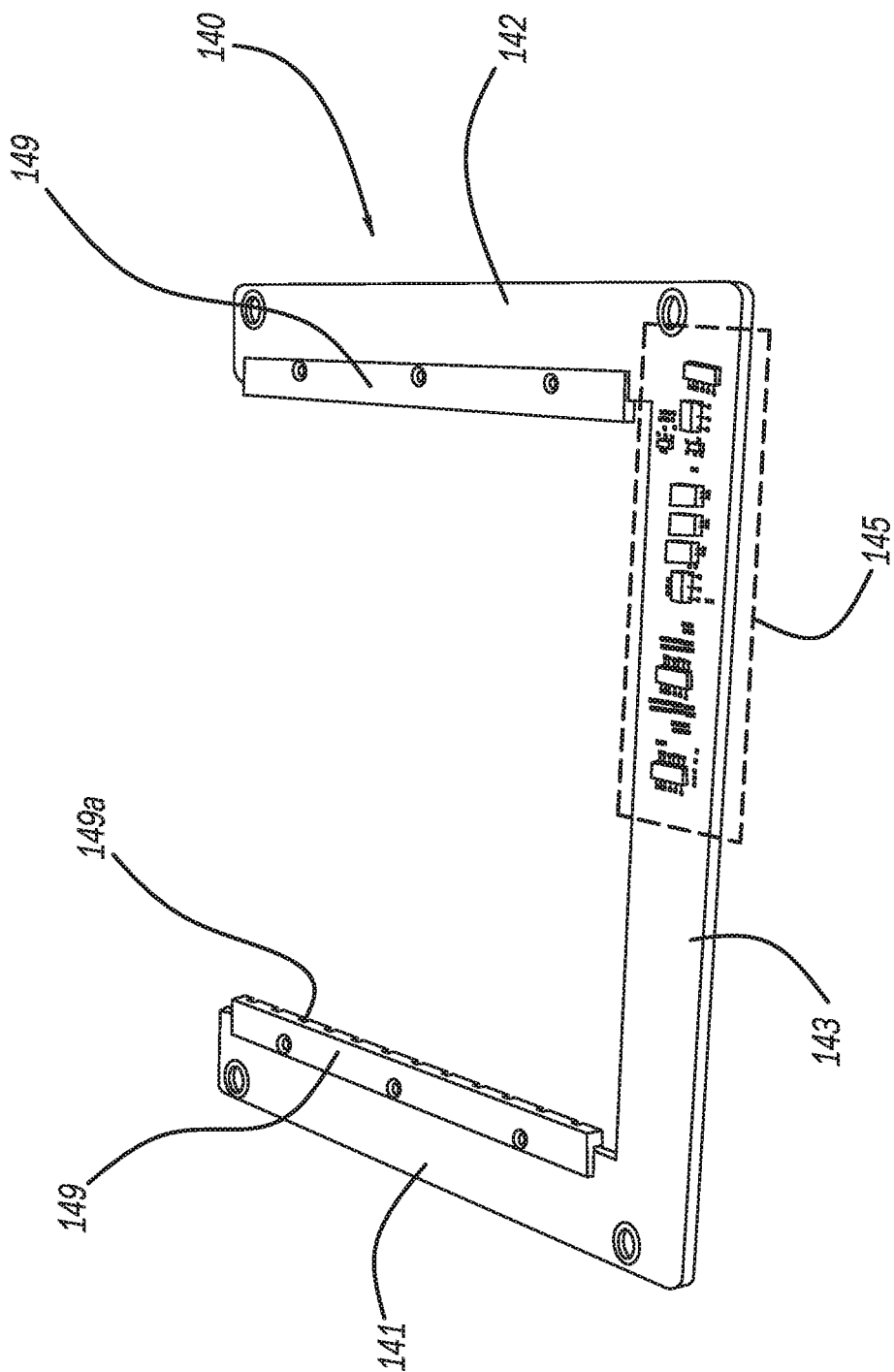

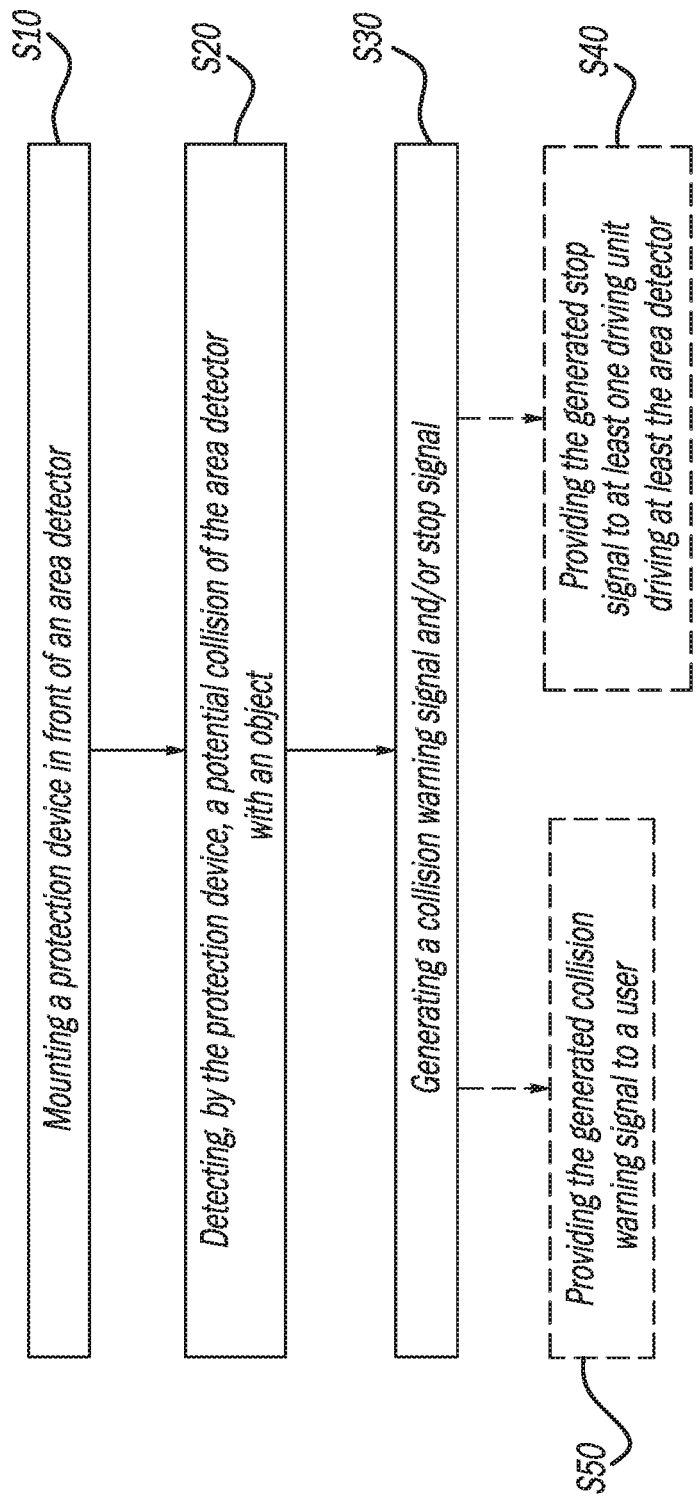

PROTECTION DEVICE FOR AN AREA DETECTOR

CROSS-REFERENCE TO RELATED APPLICATION

This application claims the benefit of priority under 35 U.S.C. § 119 to European Patent Application No. 18 195 713.5, filed Sep. 20, 2018, the contents of which are incorporated herein by reference in their entirety.

TECHNICAL FIELD

The present invention generally relates to the field of area detectors. More particularly, the invention relates to a protection device and method for protecting an area detector against collision with an object. The invention also relates to an X-ray detector system and an X-ray analysis system comprising such a protection device.

BACKGROUND

Two-dimensional area detectors (in short 2D area detectors) based on HPC, CCD or CMOS technology are nowadays widely used for detecting electromagnetic radiation. For instance, two-dimensional (or 2D) CCD or CMOS sensors can be found in cameras for capturing pictures. Large 2D HPC, CCD or CMOS sensors are also increasingly used as detectors in investigation systems, such as X-ray analysis systems. Such 2D area detectors are more convenient than conventional imaging plates since such sensors enable real time detection at high image resolution and image sensitivity.

In the field of X-ray analysis 2D area detectors having a sensitive area (i.e. sensor height×width) of greater than 150×150 mm$^2$ are nowadays commercially available. The advantage of such large area detectors is that they cover a large solid angle range enabling therefore a simultaneous detection of X-ray beams diffracted over a wide solid angle range. Accordingly, the detection time can be further shortened since the area detector must be less strongly moved in space in order to record an X-ray diffraction pattern over a wide angle range.

Large 2D area detectors have the risk that they can be easily hit and damaged by external objects. For instance, in X-ray diffraction systems 2D area detectors for X-ray detection are usually mounted on corresponding goniometer arms to be movable in angular and radial direction with respect to a sample stage and/or an X-ray source. The X-ray source and the sample stage may also be mounted (either stationary or movable) on the goniometer. As the space or distance between sample stage, 2D X-ray area detector and X-ray source may become small depending on the experimental needs, the risk for an unintentional collision of the movable area detector with the sample stage, X-ray source, a sample loading robot or any other goniometer part should not be underestimated. The risk of such an unintentional collision with the sensitive area detector is in particular high during an initial adjusting process of the X-ray analysis system where the area detector, sample stage and X-ray source are adjusted and oriented with respect to each other according to the experimental needs. This is all the more true when an unexperienced operator is carrying out such an adjusting process. As the area detectors are usually only protected by a fragile transmission window (e.g. beryllium, mylar or kapton window for X-ray detectors), the area detector can be severely damaged by such collisions.

Accordingly, it is an object of the present invention to provide a protection for such sensitive area detectors against mechanical collision. It is a further object of the present invention to provide a protection design which can be easily and cost-effectively manufactured and which can be mounted to any area detector design. It is a further object of the present invention to provide a protection device which has a compact design and which can be installed in any X-ray analysis system without hampering the functionality of the X-ray analysis system.

SUMMARY

In order to solve the above-mentioned problems and other problems, the present invention provides a protection device for protecting an area detector against collision with an object. The protection device is designed to be mountable on the area detector and comprises a mounting frame configured to be mounted on the area detector to be protected, wherein the mounting frame is designed to at least partially cover a perimeter rim surface of the area detector to be protected; a first sensor unit arranged on the mounting frame and comprising a light curtain configured to detect and signal a potential collision of the object at an inner area of the area detector surrounded by the mounting frame; and a second sensor unit arranged on the mounting frame and comprising at least one sensor configured to detect and signal a potential collision of the object at a perimeter rim area of the area detector.

The inner area of the area detector may be the sensitive detector area, i.e., the area covered by the detector sensor for detecting radiation. The rim area of the detector may be the area that surrounds the inner area and that is not sensitive for radiation.

The area detector to be protected may be a 2D X-ray detector configured to detect X-rays. The 2D X-ray detector may be designed for an X-ray analysis system, in particular an X-ray diffractometer. The 2D X-ray detector may be employed as stationary or movable detector mounted on a goniometer (or goniometer arm) of the X-ray analysis system. The X-ray area detector may comprise a semiconductor-based 2D X-ray sensor, such as a HPC, CCD or CMOS sensor. The 2D X-ray detector may further comprise a read-out electronics for reading out the 2D X-ray sensor, and a housing for receiving the 2D X-ray sensor and the corresponding read-out electronics. Further, the 2D X-ray detector may comprise a transmission window that is arranged in front of the X-ray sensor. The transmission window may be transparent for X-ray beams and arranged for protecting the sensitive X-ray sensor against the environment. It is noted that the use of the present protection device is not limited to X-ray area detectors. Rather, the protection device can be employed for any kind of area detector capable of detecting any kind of electromagnetic radiation.

In order to protect the area detector against collisions with objects, the protection device may be detachably mounted in front of the area detector (e.g., in front of the detector's transmission window). For this purpose, the mounting frame of the protection device may be designed and dimensioned in accordance with the shape and dimension of the area detector to be protected. In particular, the mounting frame may be shaped and designed such that the mounting frame in its mounted state only covers the rim portion of the area detector without covering the sensitive detector area. Further, the mounting frame may be provided with at least one quick fastening element (e.g., at least one clamp element) for fixing the mounting frame at the front side or lateral sides of the area detector (area detector housing).

The colliding object may be a stationary or a movable object, such as an X-ray generator, a goniometer on which the X-ray generator or X-ray detector can be mounted, or any other part of an X-ray analysis system, in particular an X-ray diffractometer. Hence, the area detector and colliding object may be components of an X-ray analysis system, in particular of an X-ray diffractometer, which are movable with respect to each other. Departing from the above-mentioned implementation where the area detector and colliding object are components of an X-ray analysis system, in particular of an X-ray diffractometer, the area detector of the present invention may be any kind of area detector (having any kind of area size and/or area geometry) configured to detect a desired physical quantity (for instance, electromagnetic radiation, heat radiation etc.) over a large-scale 2D area. Further, the object may be any object (movable or stationary) which may come into contact with the 2D area detector.

The protection device may further comprise at least one logic unit that is in communication with the first sensor unit and the second sensor unit. The at least one logic unit may be configured to generate at least one collision warning signal and/or at least one stop signal for the object and/or the area detector upon receiving at least one signal from the first sensor unit and/or the second sensor unit indicative of a potential collision with the area detector. In response to the at least one collision warning signal, an operator can stop the moving object and/or moving area detector, avoiding therefore a collision of the object with the area detector. Alternatively, in case the object and/or area detector are automatically driven by at least one driving unit (as it is the case in modern X-ray analysis systems), the stop signal may stop the driving unit to move further the object and/or the area detector avoiding therefore a collision of the object with the area detector. Accordingly, by generating and signalling such warning and/or stop signals to the (moving) object and/or (moving) area detector, a collision between the object and the detector can be avoided before a collision effectively takes place.

The light curtain of the first sensor unit may be formed by a plurality of light emitters and associated light receivers. The light emitters and the associated light receivers may be arranged in pairs such that each light receiver can detect a corresponding light beam transmitted by an associated light emitter. Neighbouring pairs of light emitters and light receivers may be arranged to form a light curtain with a required spatial resolution. The required spatial resolution of the light curtain can be obtained by appropriately adjusting the distance between neighbouring pairs of light emitters and light receivers (and thus the distance between neighbouring light beams of the light curtain). For instance, the pairs of light emitters and light receivers may be arranged such that the distance between neighbouring light beams is 5 mm or less in order to detect a minimum object size of 5 mm or less. If the potentially colliding object size is known to be larger than 5 mm, for example, then the pairs of light emitters and light receivers may be arranged such that the distance between neighbouring light beams is larger than 5 mm. In such a case, a distance larger than 5 mm between neighbouring light beams will be sufficient to provide the necessary resolution to detect the object.

A potential collision of an object with the area detector may be signalled by the first sensor unit when at least one light receiver of the light curtain detects an interruption or a (strong) attenuation of a corresponding light beam transmitted by the associated light emitter. Such a light beam interruption or attenuation will take place whenever an object is penetrating the light curtain. Since the protection device with the light curtain may be mounted in front of the area detector (e.g. in front of the transmission window) as explained above, a potential collision of an approaching object with the area detector can be detected and signalled in good time before an impact of the object on the detector surface will occur.

The first sensor unit comprising the light curtain consisting of an array of pairs of light emitters and light receivers may further comprise at least one collimating bar. The at least one collimating bar may comprise a plurality of collimating holes (or collimating slits) coinciding with the light emitters and light receivers. The collimating holes (or collimating slits) may be designed for collimating individually each light beam of each light emitter and collimating individually the acceptance angle of each light receiver.

The at least one sensor of the second sensor unit may be a proximity sensor. The proximity sensor may be configured and arranged on the mounting frame to detect a potential collision of the object at the perimeter rim surface of the area detector. The proximity sensor may be designed as inductive proximity sensor, capacitive proximity sensor or photoelectric proximity sensor. The proximity sensor may be able to detect the presence of a colliding object in the vicinity of the frame without getting in touch with the colliding object. Hence, the second sensor unit comprising at least one proximity sensor enables an effective protection of the rim surface of the area detector against potential collisions.

According to an alternative implementation variant the second sensor unit may be designed as mechanical sensor comprising a movable outer frame and at least one switch as second sensor. The at least one switch may be positioned between the movable outer frame on the one side and the mounting frame or any other element, such as a printed circuit board mounted on the mounting frame on the other side. The movable outer frame may be designed to activate the at least one switch arranged between the outer frame and the mounting frame when an object is colliding at the outer frame.

The at least one switch may be a micro-switch configured to be mechanically activated by the movable outer frame. The at least one micro-switch may be configured to close an electrical circuit or generate an electrical signal upon mechanical activation. When a colliding object hits against the outer frame, the outer frame may be moved towards the mounting frame activating thereby the at least one switch. The activated switch may trigger an electrical signal indicative of a collision of the object with the outer frame. The outer frame effectively protects the detector rim surface against collision with an object, since the object only hits the outer frame which is arranged (at least a few millimetres) spaced apart from the mounting frame and thus from the surface of the area detector.

For the implementation where the second sensor unit comprise an outer frame and at least one switch, the protection device may further comprise at least one resilient mounting member arranged between the outer frame and the mounting frame. The at least one resilient mounting member may be configured to resiliently mount the outer frame with respect to the mounting frame so that the outer frame can be moved between a switch activating position (i.e., a position where the outer frame is in contact with the at least one switch) and a switch releasing position (i.e., a position where the outer frame is spaced apart from the at least one switch). The at least one resilient mounting member may be designed to hold (or drive back) the outer frame in (into) the switch releasing position (i.e. into the spaced apart position) when no pressure force is exerted on the outer frame. Further, the at least one resilient mounting member may be designed to move towards switch activating position if a colliding pressure or colliding force exerted by a colliding object on the outer frame is strong enough to overcome the elastic force. The at least one resilient member may be a spring (e.g. a coil spring)

The protection device may further comprise a printed circuit board (PCB) arranged on the mounting frame. The PCB may have the shape of a frame. The shape of the PCB frame may match the shape of the mounting frame. The light emitters and associated light receivers of the light curtain may be arranged on opposite frame portions of the PCB frame. Further, the at least one second sensor may also be arranged on the PCB frame. Hence, components of the first sensor unit and second sensor unit can be integrated in a compact and cost effective way on the PCB frame.

Further provided is an X-ray detector system configured to detect diffracted X-ray beams. The X-ray detector system comprises an X-ray detector comprising a detector housing and at least one 2D X-ray sensor received within the housing; and the protection device as described above, wherein the protection device is detachably mounted in front of the 2D X-ray detector to protect the 2D X-ray sensor against collision with an object. The colliding object may be an X-ray generator, goniometer (goniometer arm), a sample loading robot, or any other moving part of an X-ray diffractometer.

The X-ray detector may further comprise an X-ray transmission window (e.g., a beryllium, mylar or kapton window) disposed in the housing in front of the 2D X-ray sensor. In such a case, the protection device may be arranged in front of the X-ray transmission window.

Provided is further an X-ray analysis system, such as an X-ray diffractometer, wherein the X-ray analysis system comprises an X-ray generator configured to generate X-rays and, the above-described X-ray detector system. The X-ray analysis system may further comprise a sample stage and a movable goniometer configured to at least move the X-ray detector to a desired angular and/or radial position with respect to the sample stage. The X-ray analysis system may also comprise at least one driving unit for moving the X-ray detector and/or goniometer (goniometer arms) of the X-ray analysis system.

According to still another aspect of the invention, a method of protecting an area detector against collision with an object is provided. The method comprises mounting the above-described protection device in front of the area detector; and detecting, by the protection device, a potential collision of the movable area detector with an object. The detector may be an X-ray detector. The object may be an X-ray source, sample stage or goniometer components of an X-ray analysis system. The detecting of a potential collision may be (continuously) performed during X-ray diffraction experiments and/or initial adjustment of the X-ray analysis system.

The method may further comprise generating a collision warning signal and/or stop signal. The method may further comprise providing the stop signal to at least one driving unit coupled to the area detector and/or goniometer for stopping movement of the area detector and/or goniometer (goniometer arms). The step of providing the stop signal to at least one driving unit may comprise providing the signal to at least one logic unit of the at least one driving unit, the at least one logic unit being configured to control the at least one driving unit and stop the at least one driving unit after receiving the stop signal.

The collision warning signal may be an optical and/or acoustical signal for signalling a potential collision of an object with the detector to a user.

BRIEF DESCRIPTION OF THE DRAWINGS

Further details, aspects and advantages of the present invention described herein will become apparent from the following drawings, in which

FIG. 2c shows a photograph of the first sensor unit of the protection device according to FIG. 1;

FIG. 5 illustrates a flow diagram of a method according to the present invention.

DETAILED DESCRIPTION

In the following description, for the purposes of explanation and not limitation, specific details are set forth in order to provide a thorough understanding of the invention presented herein. It will be apparent for one skilled in the art that the enclosed protection technique for an area detector may deviate within the scope of protection from specific details set forth hereinafter.

Figure 1:
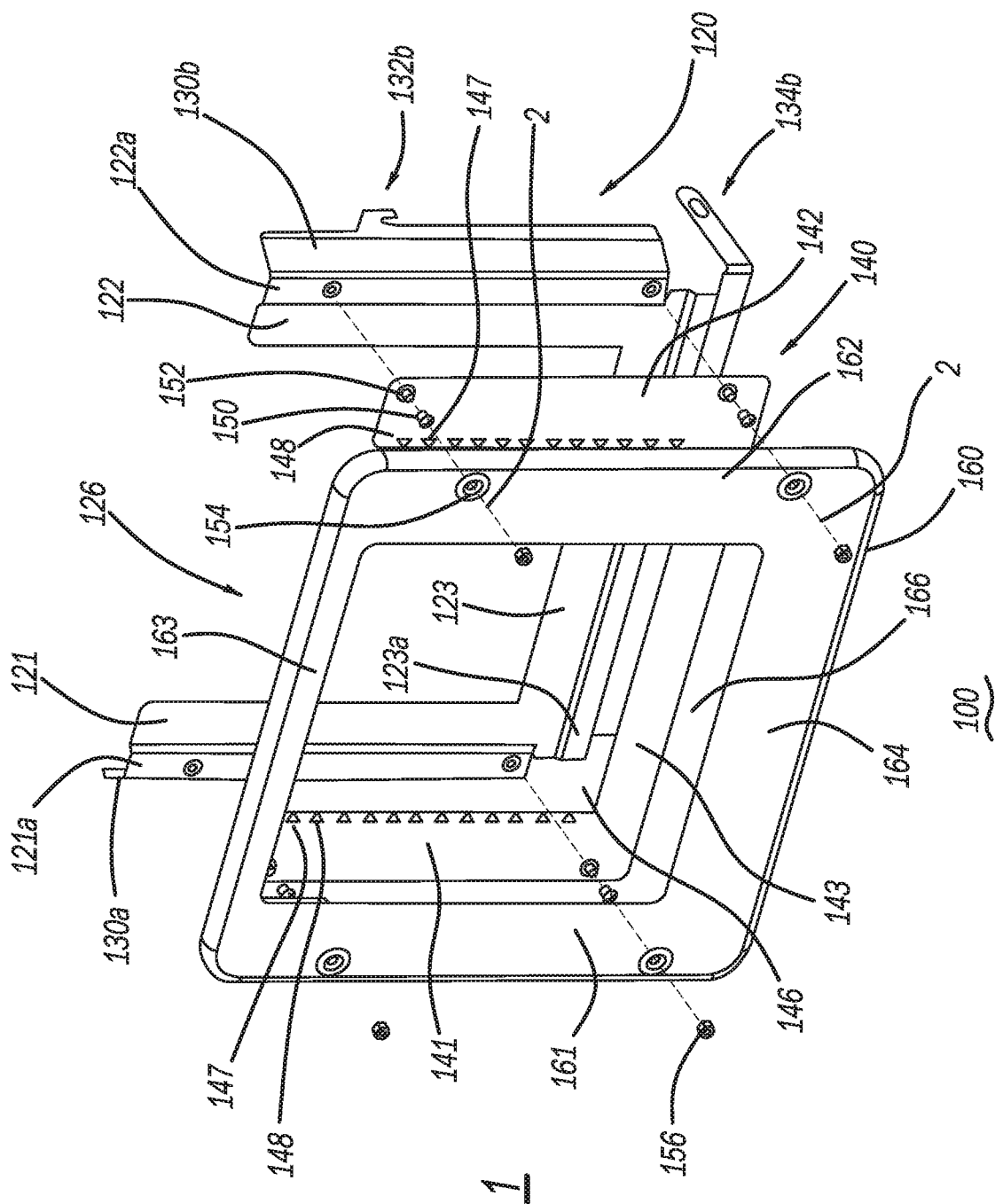
FIG. 1 illustrates a three-dimensional view of a protection device according to the present invention.

Reference is made to FIG. 1. FIG. 1 illustrates an exploded view of a protection device 100 for protecting an area detector according to the present invention. The protection device 100 comprises a mounting frame 120, a printed circuit board frame (short PCB frame) 140 and an outer frame 160.

Figure 4:
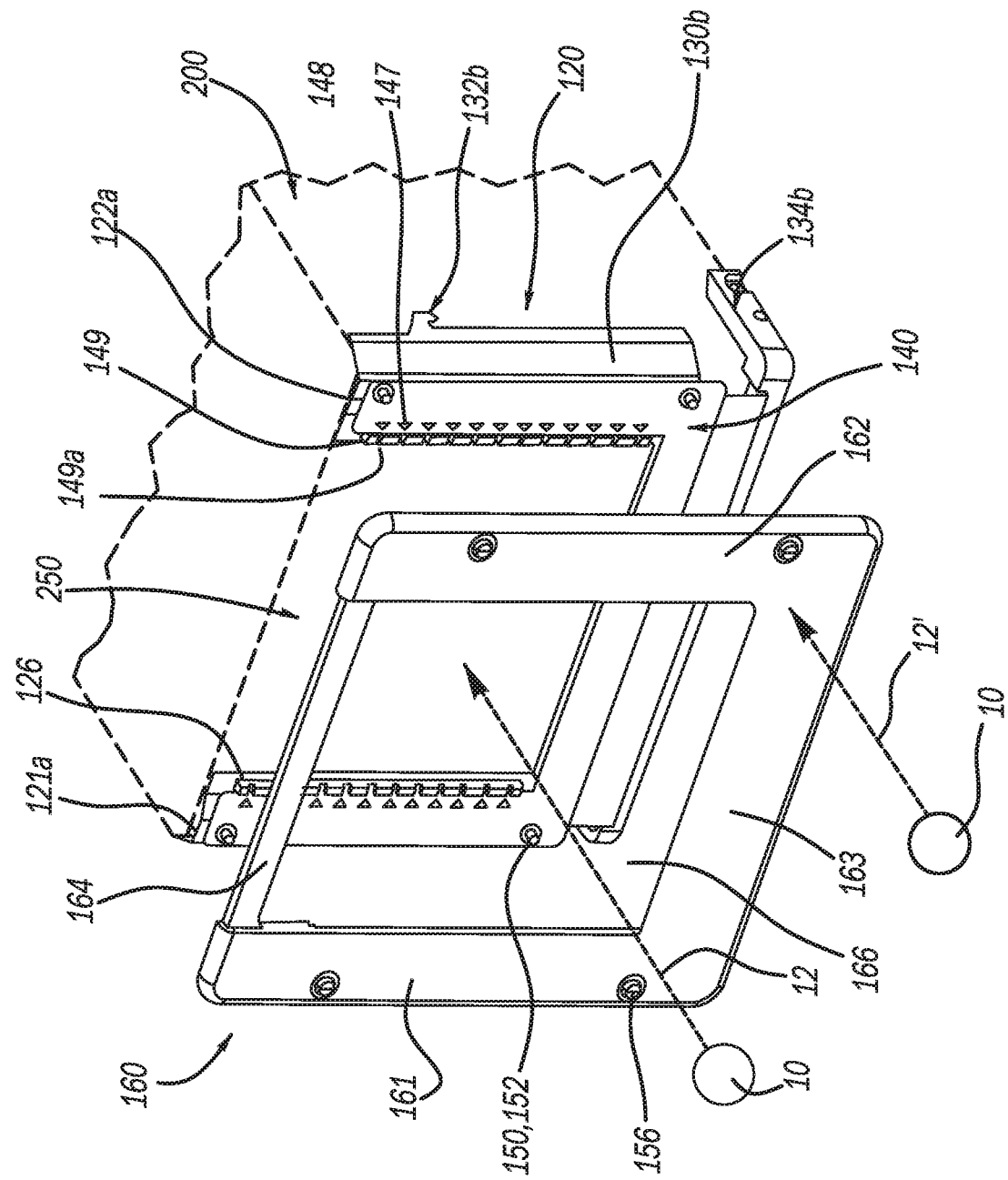
FIG. 4 illustrates the protection device of FIG. 1 in a partially assembled state.

The mounting frame 120 is designed for receiving the PCB 140 and the outer frame 160. Hence, the mounting frame 120 acts as a support frame for the PCB 140 and for the outer frame 160. Moreover, the mounting frame 120 is designed for being detachably mounted on an area detector 200 to be protected. The area detector 200 is illustrated in FIG. 4. The area detector 200 may comprise a semiconductor-based area sensor, such as a HPC-sensor, CCD-sensor or CMOS-sensor configured to detect electromagnetic radiation. According to one implementation the area detector 200 may be an X-ray detector for detecting diffracted X-ray beams.

The mounting frame 120 of the protection device 100 comprises three frame bars 121, 122, 123, which are arranged to each other to form a frame. Each of the frame bars 121, 122, 123 comprises a (slightly) elevated outer rim portion 121a, 122a, 123a on which the PCB frame 140 is mounted. The mounting frame 120 in FIG. 1 has a U-shape. The illustrated U-shape is only one exemplary frame design. Other frame shapes are conceivable. For instance, the frame 120 may have a rectangular shape with four frame bars, i.e., one frame bar per frame side. It is clear that the shape and/or dimension of the mounting frame 120 is adjusted to the shape and/or form of the area detector (front detector area) to be protected. Hence, the frame bars 121, 122, 123 are designed and dimensioned such that a mounting frame 120 can be obtained defining an inner open area 126 that substantially corresponds to the sensitive area 250 of the detector 200 (see FIG. 4). Accordingly, the frame bars 121, 122, 123 may only cover a perimeter rim area of the area detector 200 which is not sensitive to electromagnetic radiation (e.g., X-rays).

The mounting frame 120 may further comprise mounting bars 130a, 130b and mounting elements 132b, 134b that are arranged laterally with respect to the frame bars 121, 122, 123. The mounting elements 132b, 134b may be arranged symmetrically on both lateral sides of the mounting frame 120 facing each other. FIGS. 1 and 4 only illustrate the mounting elements 132b, 134b of the right lateral frame side, whereas the mounting elements of the left side are hidden by the mounting frame 120. The laterally arranged mounting bars 130a, 130b and mounting elements 132b, 134b are designed to form a mounting system so that the protection device 100 can be detachably mounted to the detector 200.

The mounting bars 130a, 130b and mounting elements 132b, 134b (and equivalent parts on the other side) are designed and dimensioned such that they correspond to the mechanical construction of the detector 200 in FIG. 4. Variations on the design and dimensions of mounting bars 130a, 130b and elements 132b, 134b would be needed for other types of detector 200.

The mounting bars 130a, 130b and mounting elements 132b, 134b may be designed as separate elements that are laterally attached to the frame bars 121, 122, 123. Alternatively, the mounting bars 130a, 130b and mounting elements 132b, 134b may be integrally formed with the frame bars 121, 122, 123, as it is shown in FIG. 1.

The protection device 100 further comprises a (single piece) PCB frame 140 that is arranged between the mounting frame 120 and the outer frame 140. The PCB frame 140 has a U-shape. The U-shaped PCB frame 140 comprises two frame portions 141, 142, which are arranged opposite each other. Moreover, the two frame portions 141, 142 are connected to each other by a PCB base portion 143 arranged on the bottom or top of the PCB frame 140. Of course, other shapes of the PCB-frame 140, e.g. a rectangular PCB-frame shape with two horizontally arranged frame portions and two vertically arranged frame portions may also be conceivable. The two horizontally arranged frame portions and the two vertically arranged frame portions are spaced-apart from each other, respectively, to form a PCB frame 140 with an inner open area 146. The PCB frame 140 formed by the PCB portions 141, 142, 143 has substantially the same form as the mounting frame 120. More specifically, the PCB frame 140 defines an inner open area 146 that has substantially the same area shape and area dimension as the inner open area 126 defined by the mounting frame 120. The area form and area dimension of the PCB frame may be adjusted to the shape and form of the area detector 200 to be protected.

The PCB frame 140 may be a part of a first sensor unit comprised by the protection device 100. The first sensor unit comprises a plurality of light emitters 147 and associated light receivers 148. The plurality of light emitters 147 and associated light receivers 148 are arranged on the oppositely arranged frame portions 141, 142 to form a light curtain in the open area 146. Since the PCB frame 140 is designed as single piece the light emitters 147 and light receivers 148 can be rigidly aligned with respect to each other so that the light beam signals do not change over time (unless a colliding object is introduced. The first sensor unit is further discussed in more detail in conjunction with FIGS. 2a, 2b and 2c below.

The protection device 100 further comprises the outer frame 160. The outer frame 160 is formed as single piece comprising two vertically arranged outer frame bars 161, 162 and two horizontally arranged outer frame bars 163, 164. The vertically arranged outer frame bars 161, 162 and the horizontally arranged outer frame bars 163, 164 are located opposite each other, respectively. The outer frame 160 formed by the frame bars 161, 162, 163, 163 defines an inner open area 166 that has substantially the same area shape and area dimension as the inner open areas 126, 146 defined by the mounting frame 120 and PCB frame 140, respectively.

One function of the outer frame 160 is a protection for the PCB frame 140 and its electronic elements (i.e., the light emitters 147, and light receivers 148) and electrical cable connections from colliding objects and the environment.

The outer frame 160 is part of a second sensor unit which further comprises resilient mounting members and mechanical switches (not shown in FIG. 1). The mechanical switches are micro-switches that are arranged on the PCB frame side facing towards the outer frame 160. The mechanical switches are configured to generate an electrical signal upon activation by the outer frame 160. Further, the resilient mounting members may be designed as springs 150 having a predefined spring force. The protection device 100 of FIG. 1 comprises four springs 150 that are received by corresponding pins 152 arranged on the PCB frame side facing towards the outer frame 160. The pins 152 in turn may be movably received by corresponding throughholes 154 formed in the outer frame 160, when the protection device 100 is mounted. Hence the outer frame 160 can be resiliently mounted to the PCB frame 140 (or the underlying mounting frame 120) through the springs 150. The mounting direction of the outer frame 160 and the PCB frame 140 with respect to the mounting frame 120 is illustrated by arrows 2 in FIG. 1. The functioning of the second sensor unit will further be described in more detail in conjunction with FIG. 4.

Figure 2A:
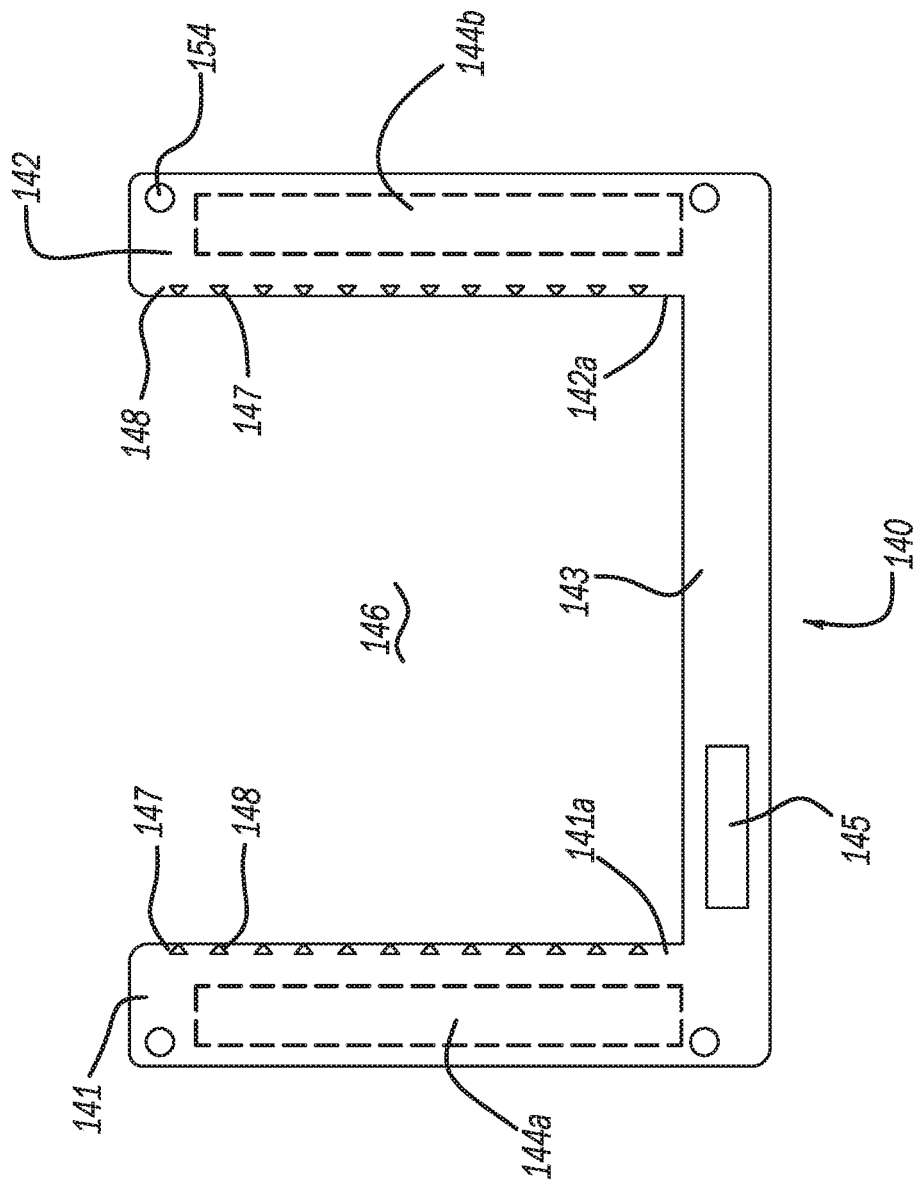
FIG. 2a illustrates components of a first sensor unit of the protection device of FIG. 1.
Figure 2B:
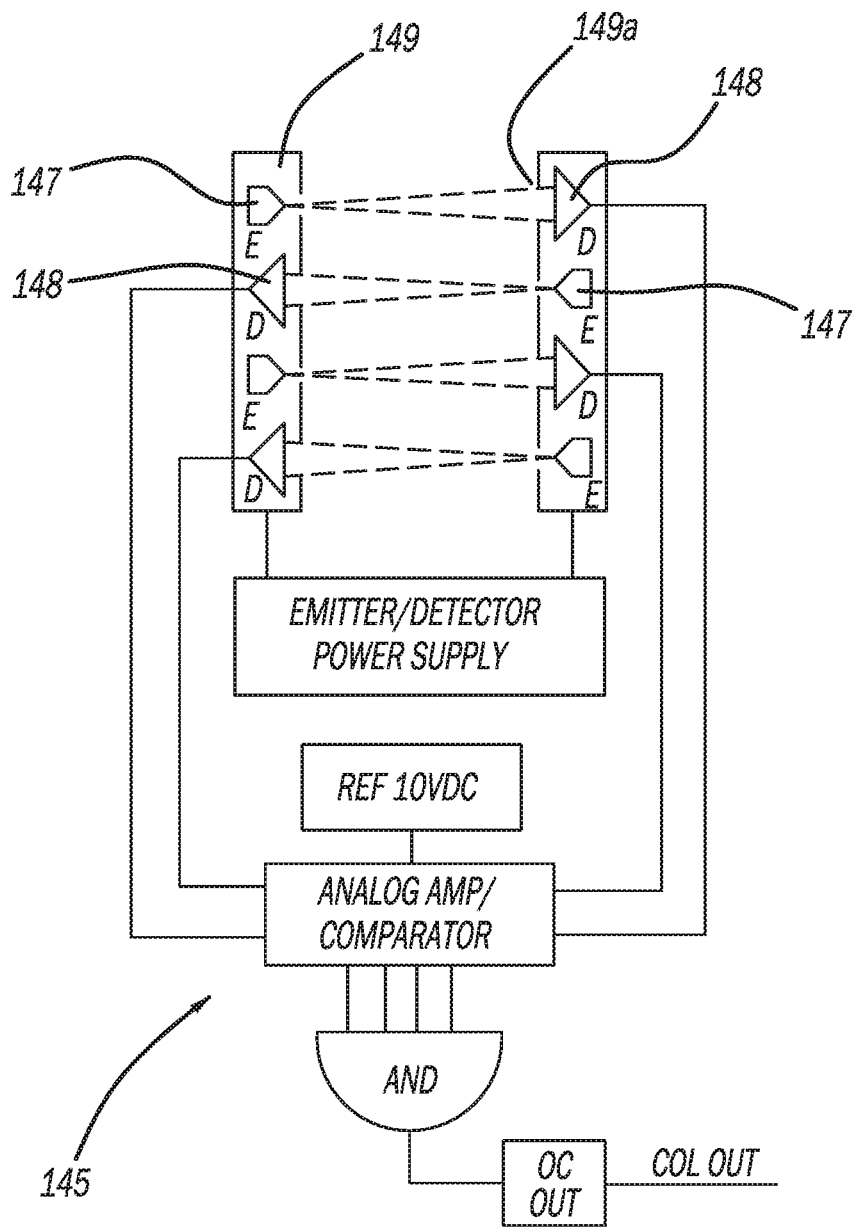
FIG. 2b illustrates a functional diagram of the first sensor unit of the protection device according to FIG. 1.

In conjunction with FIGS. 2a, 2b and 2c, the first sensor unit will be further described. FIG. 2a illustrates the PCB frame 140. On the PCB frame 140 the plurality of light emitters 147 and light receivers (or light detectors) 148 are arranged opposite each other to form corresponding emitter-receiver pairs. The emitter-receiver pairs are arranged on the PCB frame 120 such that the light beams between each emitter-receiver pair (and therefore all beams of the light curtain) run substantially parallel to the PCB frame surface. As light emitters 147 infrared emitting diodes (short IR diodes) may be used. Each IR diode may be configured to emit a (pulsed or continuous) infrared light beam (short IR beam) to the receiver 148. As light receivers 148 infrared detecting phototransistors (short IR phototransistors) may be used. Each IR phototransistor is configured to detect the (pulsed or continuous) IR beam generated by the associated IR diode.

As further illustrated in FIG. 2a, the light emitters 147 and light receivers 148 are alternatively arranged on the PCB frame portions 141, 142. For each light emitter 147 (light receiver 148) arranged on PCB frame portion 141 there is provided an associated light receiver 148 (light emitter 147) on PCB frame portion 142. Thus, light emitted by a light emitter 147 arranged on PCB frame portion 141 (or PCB frame portion 142) is detected by the associated light receiver 148 arranged directly opposite to the light emitter 147 on PCB frame portion 142 (or PCB frame portion 141)

(see FIG. 2b). The so formed pairs of light emitters 147 and light receivers 148 are arranged along the oppositely arranged PCB frame portions 141, 142 so that a light curtain is formed which covers the whole open area 146 surrounded by the PCB frame 140. Since the open area 146 substantially corresponds to the sensitive detector area 250, the sensitive detector area 250 is fully covered by the light curtain.

As further illustrated in FIGS. 1 and 2a, the light emitters 147 and light receivers 148 can be arranged in the vicinity of the inner edges 141a, 142a of the corresponding PCB portions 141, 142. Accordingly, there is enough space free on the PCB frame portions 141, 142 (see frame areas 144a, 144b in FIG. 2a) and on the frame portion 143 which can be used for arranging further sensor components. For instance, the frame areas 144a, 144b can be used for arranging one or a plurality of micro-switches for the second sensor unit. Further, the space on the frame portion 143 can be used in order to implement one or more logic units 145 (see also FIG. 2c) configured to evaluate the signals from the light receivers of the first sensor unit and/or the signals from the micro-switches of the second sensor unit. Hence the illustrated PCB frame design facilitates a compact protection device design since all essential electronic components of the first sensor unit and second sensor unit can be integrated on the PCB frame 140.

The light curtain of the first sensor unit has been primarily discussed in conjunction with the U-shaped PCB frame 140 where a plurality of light emitters 147 and associated light receivers 148 are arranged on oppositely arranged horizontal frame portions 141, 142. The present invention shall not be limited to such a light curtain design. For instance, if the PCB frame 140 has a rectangular shape with two horizontally arranged frame portions and two vertically arranged frame portions, it is also conceivable that the plurality of light emitters 147 and associated light receivers 148 are arranged on the two oppositely arranged vertical frame portions to form a light curtain with vertically aligned light beams. Further, if the PCB frame 140 has a rectangular shape it is also conceivable to arrange a first subset of the plurality of light emitters 147 and associated light receivers 148 on the two oppositely arranged horizontal frame portions and a second subset of the plurality of light emitters 147 and associated light receivers 148 on the two oppositely arranged vertical frame portions to form a light curtain with horizontally and vertically arranged light beams. By having a light curtain with horizontally and vertically arranged light beams the detection accuracy can be further improved.

The technical functionality of the light curtain generated by corresponding pairs of light emitters 147 and light receivers 148 will be further discussed in conjunction with FIG. 2b. FIG. 2b illustrates a block diagram showing the arrangement of pairs of light emitters 147 and light receivers 148 on the oppositely arranged PCB frame portions 141, 142. The distance between neighbouring pairs of light emitters 147 and light receivers 148 on the PCB frame portions 141, 142 is adjusted depending on the spatial resolution to be achieved by the light curtain. According to one implementation, the distance between neighbouring pairs of light emitters 147 and light receivers 148 may be preset such that a resolution threshold of less than or equal to 5 mm can be achieved. That means that only objects having a diameter smaller than the resolution threshold can pass the light curtain without being detected. According to another implementation, the distance between neighbouring pairs of light emitters 147 and light receivers 148 may be preset such that the resolution threshold of the light curtain is larger than 5 mm, if the potentially colliding object size is known to be larger than 5 mm.

Since the spatial resolution of the light curtain depends on the distance between neighbouring pairs of light emitters 147 and light receivers 148 and since the light emitters 147 and light receivers 148 have certain dimensions, the resolution of the light curtain may be limited by the dimensions of the used light emitters 147 and light receivers 148. In order to achieve the closest possible arrangement of the light emitters 147 and light receivers 148 on the PCB frame 140, neighbouring light emitters 147 and light receivers 148 may be arranged staggered in two lines on the PCB frame 140.

In order to operate the light curtain, at least one power supply is provided that feeds the light emitters 147 and light receivers 148 of the light curtain. Further, a logic unit 145 is provided which is in communication with each light receiver 148 of the light curtain. The logic unit 145 can be integrated on the PCB frame 140 as illustrated in FIGS. 2a and 2c. The logic unit 145 may comprise an analogue signal amplifier and a signal comparator configured to amplify and compare the signal detected by each of the light receivers 148 of the light curtain with a reference signal (e.g., a 10 V DC reference signal). Alternatively, if no reference signal is available it is also conceivable that the detected signals received from the different light receiver 148 are compared with one another. If the signal comparison with one another or with the reference signal shows a (strong) light attenuation in one or more detected light signals, collision of an object with the light curtain is signalled. Hence, with the light curtain of the first sensor unit it is possible to detect an object which is going through the open area 146 covered by the light curtain As already mentioned above, the spatial resolution of the light curtain depends on the distance between neighbouring pairs of light emitters 147 and light receivers 148. Beside the distance there is a further parameter which may affect the resolution of the light curtain. This parameter is the angular beam spread of the light beam generated by each light emitter 147. In case the light beam of each light emitter 147 spreads across a larger angular range, crosstalk effects can be observed. That is, the signal of a specific light receiver 148 is not only affected by the light beam generated by the associated light emitter 147 arranged exactly opposite the light receiver 148, but also by neighbouring light emitter 147 arranged offside the light receiver 148. In such a case the colliding object would be detected only if it breaks or (strongly) attenuates multiple light beams from the opposite light emitter 147 and also some number of offside light emitters 147, which practically means that the colliding object would need to be larger, and thus the resolution of the light curtain would be reduced.

In order to reduce crosstalk effects, the distance between neighbouring light emitters 147 and neighbouring light receivers 148 may be doubled by alternating their mounting positions between PCB frame portions 141 and 142, instead of mounting all light emitters 147 side by side on one PCB frame portion 141 and all light receivers 148 side by side on the opposing PCB frame portion 142, as illustrated in FIGS. 1, 2a and 2b.

In order to further reduce crosstalk effects, the first sensor unit may further comprise collimating bars 149 (see FIGS. 2b and 2c). The collimating bars 149 may comprise a plurality of holes (or slits) 149a which coincide with the position of the light emitters 147 and light receivers 148. For this purpose, a collimating bar 149 is arranged along each of the inner edges of the PCB frame portions 141, 142 such that the position of the holes coincides with the position of the respective light emitter 147 and light receivers 148 (see FIGS. 2a and 2c). Hence, the collimating bars 149 with the collimating holes 149a are provided for collimating individually each light beam of each light emitter 147 and for collimating individually the acceptance angle of each light receiver 148.

Figure 3A:
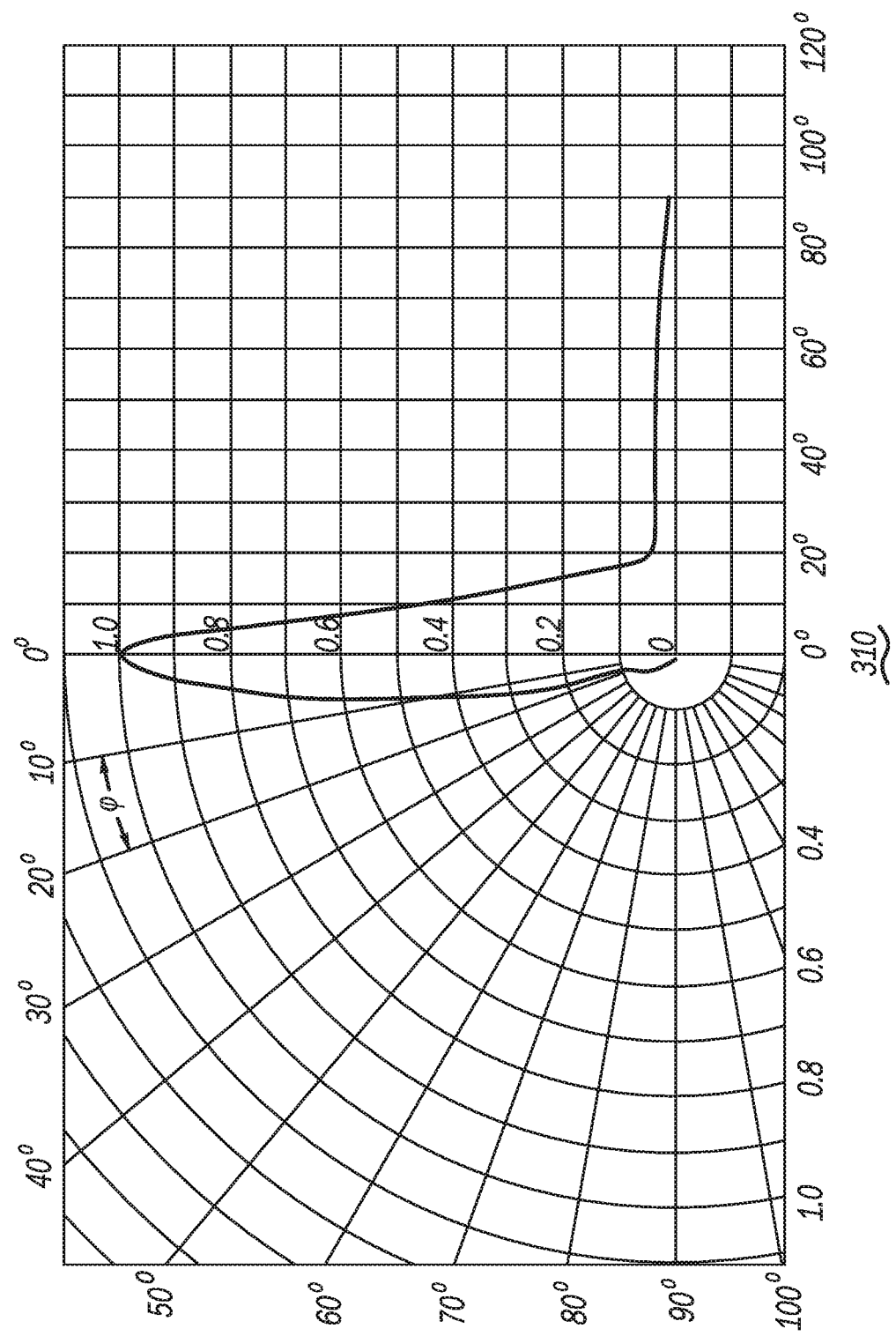
FIGS. 3a-3b illustrate an angular distribution of the light beams of the first sensor unit.
Figure 3B:
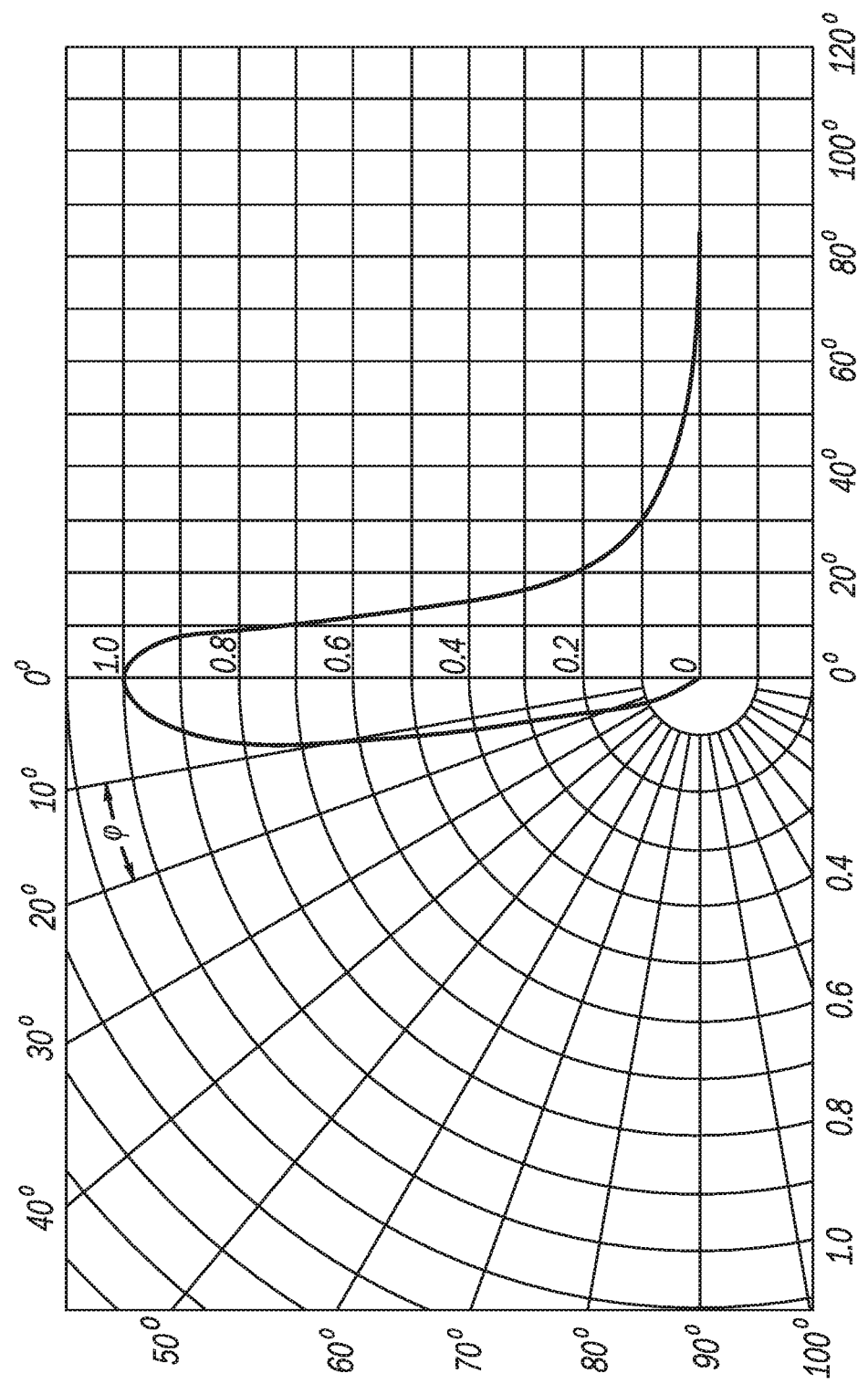

The angular distribution of the collimated light beams and collimated acceptance angles are illustrated in FIGS. 3a and 3b. FIG. 3a shows a plot 310 illustrating the angular intensity distribution of the light beam from light emitter 147. As can be derived from plot 310, the angular distribution of the normalized light beam intensity decreases rapidly for angles different from 0 degree, wherein the angles are measured with respect to an imaginary line that directly connects a corresponding pair of light emitter 147 and light receiver 148 arranged opposite each other. The electronic component of the light emitter 147 has to be well chosen to have this angular width as small as possible. By passing the light beam through holes 149a of the collimating bar 149 this angular width is even further narrowed. Hence the collimating bar 149 generates highly collimated light beams so that crosstalk between neighbouring light emitters 147 can be reduced. In a similar way, as derivable from plot 320 shown in FIG. 3b, the acceptance angle for each light receiver 148 is also narrow due to the well-chosen electronic component. That angular acceptance range is further narrowed to a smaller angular range by placing the collimating hole 149a of the collimating bar 149 directly in front of the light receiver 148. That is, light beams with large incident angles are cut away and cross talk is minimised.

As derivable from FIG. 4, the PCB frame 140 is mounted on the mounting frame 120. For instance, the PCB frame 140 can be glued or otherwise fixed to the mounting frame front side. Since the PCB frame 140 implementing the light curtain is mounted on the elevated outer rim portions 121a, 122a, 123a of the mounting frame 120, the light curtain is arranged sufficiently spaced apart from the inner open area 126 defined by the mounting frame 120. Accordingly, a colliding object 10 which moves through the open area 166 of the outer frame (arrow 12 in FIG. 4 indicates this movement) can be detected by the light curtain and stopped before the object 10 passes the inner open area 126 of the mounting frame 120 and hits the detector 200 on its sensitive front area 250.

The outer frame 160, in turn, is resiliently mounted through the springs 150 to the PCB frame 140 or to the mounting frame 120. Retaining elements 156 (e.g., screws) may be provided configured to hold the outer frame 160 in a releasing position, i.e., a position where the outer frame does not touch (or activate) the micro-switches mounted on the underlying PCB frame 140. The outer frame 160 has two functionalities. The first functionality consists in a sensing functionality since a collision of the object 10 with the outer frame 160 (see arrow 12' in FIG. 4 indicating the collision with the outer frame) moves the outer frame 160 towards the PCB and activates the micro-switches thereon.

The second functionality consists in a protection functionality because the outer frame 10 protects the underlying PCB 140 and the detector 200 against the environment and object's collisions. In particular object's collisions are damped by the spring-mounted outer frame 160.

In conjunction with FIG. 5 a use of the above-described protection device 100 will be further discussed. FIG. 5 illustrates a flow diagram of a method of protecting an area detector 200, as illustrated in FIG. 4. The area detector 200 may be an X-ray area detector for use in an X-ray analysis system (not shown in FIG. 4).

According to a first method step S10, the protection device 100 is mounted in front of the area detector 200. The mounting may be performed through the mounting elements 132b, 134b (see FIG. 4) arranged on both mounting bars 130a, 130b. In FIG. 4 only the mounting elements 132b, 134b for the right-hand mounting bar 130b are visible, while the corresponding mounting elements 132b, 134b for the left-hand mounting bar 130a are hidden. As illustrated in FIG. 4, the protection device 100 is mounted in front of the area detector 200 so that the frame-like protection device 100 only covers a small rim area of the detector 200 and leaves fully open the sensitive area 250. Hence, the mounted protection device 100 does not adversely affect the radiation detection of the detector 200. Moreover, the mounting elements 132b, 134b are designed such that the whole protection device 100 can be detachably mounted at lateral sides of the detector housing.

After the protection device 100 has been mounted in front of the detector 200, in a subsequent second step S20 the protection device 100 detects potential collisions of the area detector 100 with an object 10. The detection step can be performed continuously during detector measurement and/or during an initial detector adjustment procedure. The detecting may comprise reading out the signals of the first sensor unit and/or second sensor unit of the protection device 100 and comparing the read-out signals of the first sensor unit and/or second sensor unit with corresponding reference signals (for instance, reference voltages). If the read-out signals of the first sensor unit and/or second sensor unit deviate from the corresponding reference values, a collision warning signal and/or stop signal may be generated in a subsequent third step S30.

According to one implementation of the method illustrated in FIG. 5, the generated stop signal may be provided to at least one driving unit configured to drive the area detector (step S40). The step of providing the stop signal to at least one driving unit may comprise providing the signal to at least one logic unit of the at least one driving unit. The at least one logic unit may be configured to control the at least one driving unit and stop the at least one driving unit after receiving the stop signal.

Alternatively or in addition to method step S40 the generated collision warning signal may be provided to a user (step S50) in order to warn the user of a potential collision of the detector 200 with an object. The user can then stop the movement of the detector 200.

The above-described protection device 100 has the following advantages. The frame-like design of the protection device 100 can be easily manufactured and installed on any area detector (or detector housing). Further, the protection device 100 shows a high integration of the detector components as the light emitters 147 and light receivers 148 of the first sensor unit as well as the micro-switches of the second sensor unit are all arranged on the PCB frame 140. Accordingly, a compact design is achieved that only needs little space for protecting the sensitive front surface of the detector and that does not hamper the functionalities of an analysis system, such as an X-ray analysis system.

While the above description constitutes the preferred embodiment of the present invention, it will be appreciated that the invention is susceptible to modification, variation and change without departing from the proper scope and fair meaning of the accompanying claims.

The invention claimed is:
1. A protection device for protecting an area detector against collision with an object, wherein the protection device is designed to be mountable on the area detector, the protection device comprising:
- a mounting frame configured to be mounted on the area detector, wherein the mounting frame at least partially covers a perimetral rim surface of the area detector to be protected;
- a first sensor unit arranged on said mounting frame and comprising a light curtain configured to detect and signal a potential collision of the object at an inner surface of the area detector surrounded by the mounting frame; and
- a second sensor unit arranged on said mounting frame and comprising at least one sensor configured to detect and signal a potential collision of the object at the perimetral rim surface of the area detector.

2. The protection device according to claim 1, wherein the area detector to be protected is a 2D X-ray detector of an X-ray analysis system.

3. The protection device according to claim 2, wherein the object is an X-ray generator, a goniometer, or any other moving part of an X-ray diffractometer.

4. The protection device according to claim 1, wherein the object is an X-ray generator, a goniometer, or a moving part of an X-ray diffractometer.

5. The protection device according to claim 1, further comprising at least one logic unit that is in communication with the first sensor unit and the second sensor unit, wherein the at least one logic unit is configured to generate a collision warning signal or a stop signal for the object or area detector upon receiving the potential collision signalling from the first sensor unit or second sensor unit.

6. The protection device according to claim 1, wherein the potential collision with the object at the inner surface of the area detector is signalled when at least one light receiver of the light curtain detects an interruption or attenuation of at least one light beam transmitted by at least one associated light emitter.

7. The protection device according to claim 1, wherein the light curtain of the first sensor unit is formed by a plurality of light emitters and associated light receivers, wherein the light emitters and the associated light receivers are arranged in pairs such that each of the light receivers detects a light beam transmitted by an associated of the light emitters.

8. The protection device according to claim 7, wherein neighbouring pairs of the light emitters and the light receivers are arranged to form the light curtain with a required spatial resolution.

9. The protection device according to claim 7, wherein the first sensor unit further comprises a collimating bar, the collimating bar comprising a plurality of holes coinciding with the light emitters and light receivers and being provided for collimating individually each light beam of each light emitter and collimating individually the acceptance angle of each light receiver.

10. The protection device according to claim 7, further comprising a printed circuit board (PCB) arranged on the mounting frame, wherein the printed circuit board has a shape of a frame and wherein the light emitters and the associated light receivers of the light curtain are arranged on opposite frame portions of the printed circuit board frame.

11. The protection device according to claim 10, wherein the at least one second sensor is arranged on the printed circuit board frame.

12. The protection device according to claim 1, wherein the at least one sensor of the second sensor unit is a proximity sensor configured and arranged on the frame to detect a potential collision of the object along the perimetral rim surface of the area detector.

13. The protection device according to claim 1, wherein the second sensor unit comprises a movable outer frame and at least one sensing switch, the outer frame at least partially covers the mounting frame and the first sensor unit, and wherein the second sensor unit is configured to detect and signal the collision of the object at the perimetral rim surface of the area detector when the colliding object moves the movable outer frame towards the mounting frame thereby activating the at least one sensing switch.

14. The protection device according to claim 13, further comprising at least one resilient mounting member arranged between the outer frame and the mounting frame and configured to resiliently mount the outer frame with respect to the mounting frame so that the outer frame is moved between a non-activated position and an activated position.

15. The protection device according to claim 14, wherein the at least one sensing switch is a micro-switch configured to be mechanically activated by the movable outer frame, and to close an electrical circuit or generate an electrical signal upon mechanical activation.

16. The protection device according to claim 13, wherein the at least one sensing switch is a micro-switch configured to be mechanically activated by the movable outer frame, and to close an electrical circuit or generate an electrical signal upon a mechanical activation.

17. An X-ray detector system configured to detect diffracted X-ray beams, wherein the X-ray detector system comprises:
- an X-ray detector comprising a detector housing, and at least one 2D X-ray sensor received within the detector housing; and
- the protection device according to claim 1, wherein the protection device is detachably mounted in front of the 2D X-ray detector to protect the at least one 2D X-ray sensor against the collisions with the object in the form of an X-ray generator, a goniometer, or other moving part of an X-ray diffractometer.

18. An X-ray analysis system, wherein the X-ray analysis system comprises:
- an X-ray generator configured to generate X-rays; and
- the X-ray detector system of claim 17.

19. A method of protecting an area detector against collisions with an object, wherein the method comprises:
- providing and mounting the protection device according to claim 1 in front of the area detector; and
- detecting, by the protection device, a potential collision of the area detector with an object.

20. The method of claim 19, further comprising:
- generating a collision warning signal and/or stop signal; and
- feeding the stop signal to at least one driving unit coupled to the area detector or goniometer for stopping movement of the area detector or the goniometer.

* * * * *